United States Patent
Stevenson et al.

(10) Patent No.: US 6,567,259 B2
(45) Date of Patent: May 20, 2003

(54) MONOLITHIC CERAMIC CAPACITOR WITH BARIUM TITINATE DIELECTRIC CURIE POINT OPTIMIZED FOR ACTIVE IMPLANTABLE MEDICAL DEVICES OPERATING AT 37° C.

(75) Inventors: Robert A. Stevenson, Canyon Country, CA (US); Donald K. Haskell, Flagstaff, AZ (US); John E. Roberts, Carson City, NV (US)

(73) Assignee: Greatbatch-Sierra, Inc., Canyon Country, CA (US)

( * ) Notice: Subject to any disclaimer, the term of this patent is extended or adjusted under 35 U.S.C. 154(b) by 0 days.

(21) Appl. No.: 10/251,672

(22) Filed: Sep. 20, 2002

(65) Prior Publication Data

US 2003/0053284 A1 Mar. 20, 2003

Related U.S. Application Data

(63) Continuation-in-part of application No. 09/872,092, filed on May 31, 2001, now Pat. No. 6,456,481.

(51) Int. Cl.$^7$ ................................................ H01G 4/35
(52) U.S. Cl. ..................... 361/302; 361/306.1; 361/303
(58) Field of Search ............................ 361/302, 306.1, 361/303, 328, 329, 330; 333/182, 184, 185

(56) References Cited

U.S. PATENT DOCUMENTS

| | | |
|---|---|---|
| 2,756,375 A | 7/1956 | Peck |
| 3,235,939 A | 2/1966 | Rodriguez et al. |
| 3,538,464 A | 11/1970 | Walsh |
| 3,920,888 A | 11/1975 | Barr |
| 4,083,022 A | 4/1978 | Nijman |

(List continued on next page.)

FOREIGN PATENT DOCUMENTS

EP  1 191 556 A2 * 3/2002

OTHER PUBLICATIONS

Dual Electrode Plate MLC for High Voltage Pulse Applications, Capacitor and Resistor Technology Symposium (CARTS), Huntington Beach, California, Mar. 6–10, 2000.
Title: A Capacitor's Inductance: Critical Property for Certain Applications, IEEE 49th Electronic Components & Technology Conference (IEEE–ECTC), San Diego, California, Jun. 1–4, 1999.
Title: Design and Application of Broadband Ceramic Feed–Through Capacitor EMI Filters to Cardiac Pacemakers and Implantable Defibrillators, Robert A. Stevenson, P.E., 5 pages, Oct. 30 to Nov. 2, 1997.
Title: Radically New Internally Grounded Feedthrough Capacitor, Bob Stevenson and Rick Brendel, 8 pages, Mar. 25–30, 2001.

Primary Examiner—Anthony Dinkins
(74) Attorney, Agent, or Firm—Kelly Bauersfeld Lowry & Kelley, LLP

(57) ABSTRACT

A feedthrough filter capacitor assembly for use in active implantable medical devices and a related process for manufacturing a monolithic ceramic capacitor utilizing dielectric materials having a dielectric constant greater than 7000, and preferably in the range of 8500 to 22,000. In the manufacture of the monolithic ceramic capacitor, one or more Curie point shifters and/or other dopants are added to the dielectric material to optimize the dielectric constant at the human body temperature of 37° C. For manufacturing purposes, dopants may be added to the dielectric material to broaden the Curie point peak or point of maximum dielectric constant thereof. The effect is that when such capacitors and terminal assemblies are utilized in a high-voltage defibrillator circuit of an implantable medical device, the dielectric material is optimized so that during the delivery of high-voltage electrical energy, capacitance value of the capacitor drops substantially.

31 Claims, 13 Drawing Sheets

U.S. PATENT DOCUMENTS

| | | |
|---|---|---|
| 4,144,509 A | 3/1979 | Boutros |
| 4,148,003 A | 4/1979 | Colburn et al. |
| 4,152,540 A | 5/1979 | Duncan et al. |
| 4,220,813 A | 9/1980 | Kyle |
| 4,247,881 A | 1/1981 | Coleman |
| 4,314,213 A | 2/1982 | Wakino |
| 4,352,951 A | 10/1982 | Kyle |
| 4,362,792 A | 12/1982 | Bowsky et al. |
| 4,421,947 A | 12/1983 | Kyle |
| 4,424,551 A | 1/1984 | Stevenson et al. |
| 4,456,786 A | 6/1984 | Kyle |
| 4,737,601 A | 4/1988 | Gartzke |
| 4,741,710 A | 5/1988 | Hogan et al. |
| 5,032,692 A | 7/1991 | DeVolder |
| 5,070,605 A | 12/1991 | Daglow et al. |
| 5,142,430 A | 8/1992 | Anthony |
| 5,333,095 A | 7/1994 | Stevenson et al. |
| 5,440,447 A | 8/1995 | Shipman et al. |
| 5,670,063 A | 9/1997 | Hegner et al. |
| 5,751,539 A | 5/1998 | Stevenson et al. |
| 5,825,608 A | 10/1998 | Duva et al. |
| 5,905,627 A | 5/1999 | Brendel et al. |
| 5,959,829 A | 9/1999 | Stevenson et al. |
| 5,973,906 A | 10/1999 | Stevenson et al. |
| 5,978,204 A | 11/1999 | Stevenson |
| 6,008,980 A | 12/1999 | Stevenson et al. |
| 6,275,369 B1 | 8/2001 | Stevenson et al. |
| 6,349,025 B1 | 2/2002 | Fraley et al. |
| 6,424,234 B1 | 7/2002 | Stevenson |
| 6,456,481 B1 | 9/2002 | Stevenson |

\* cited by examiner

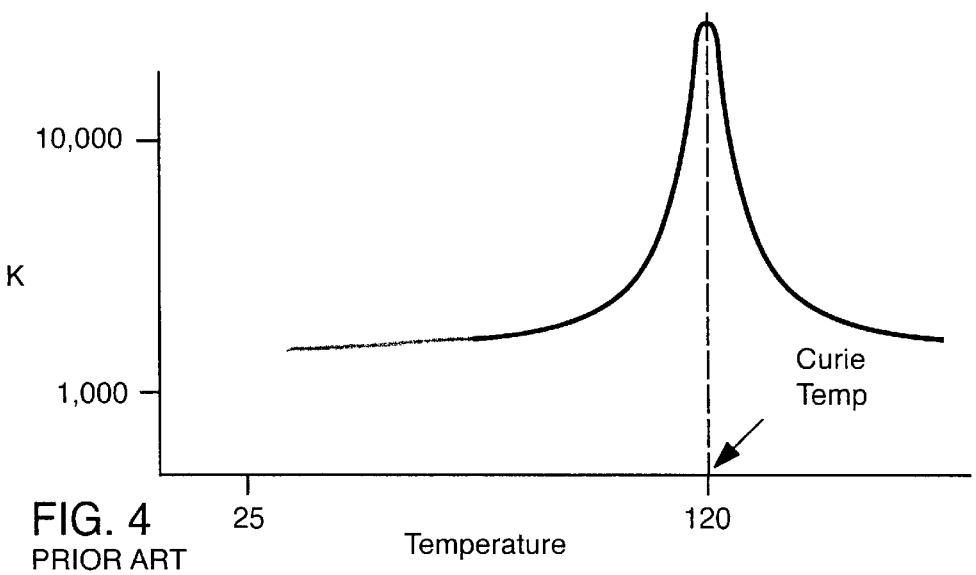
FIG. 3 PRIOR ART
FIG. 4 PRIOR ART
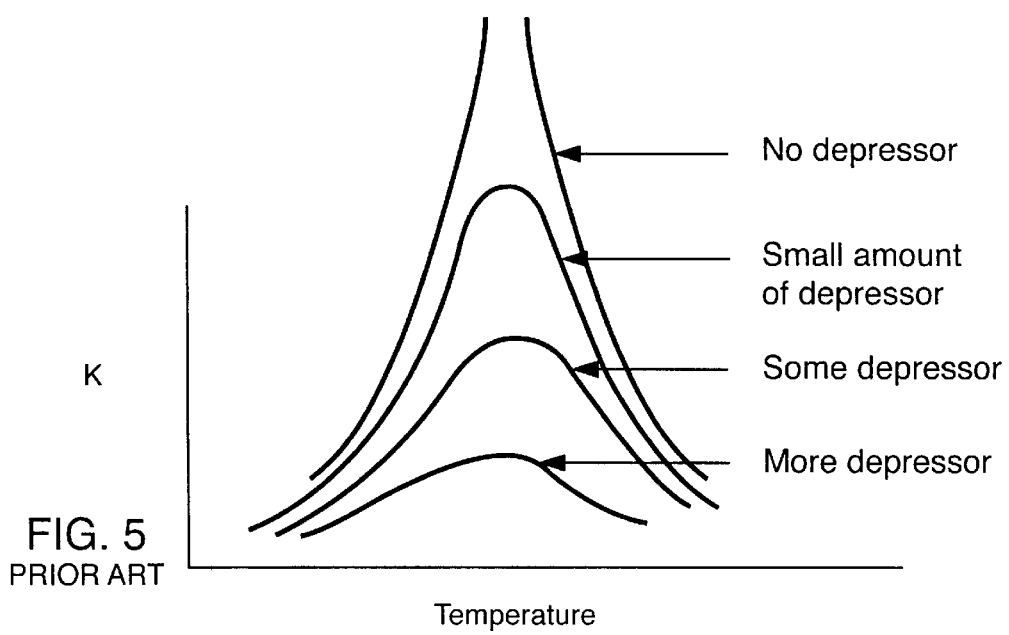
FIG. 5 PRIOR ART

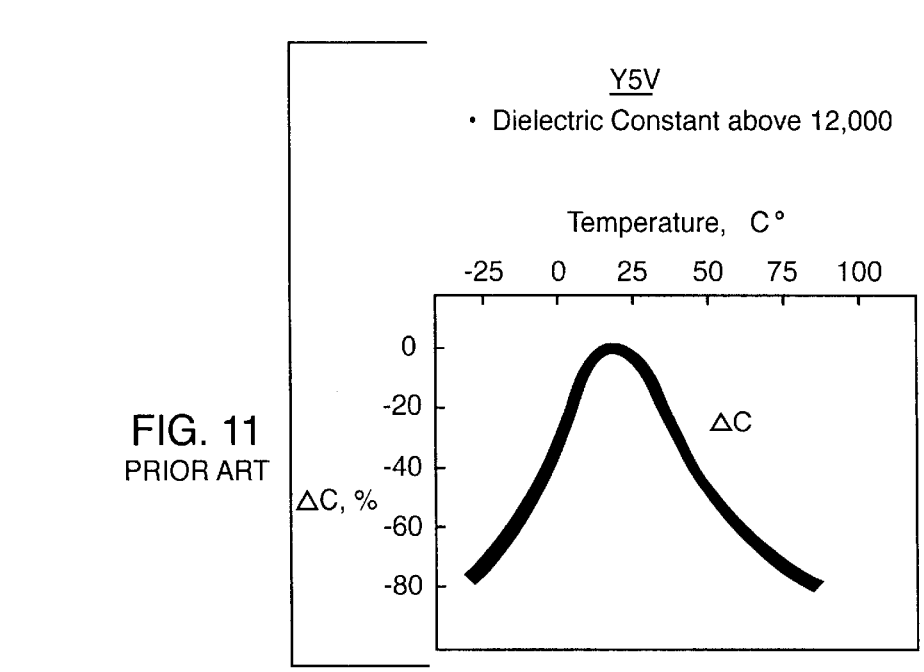
FIG. 10 PRIOR ART
FIG. 11 PRIOR ART
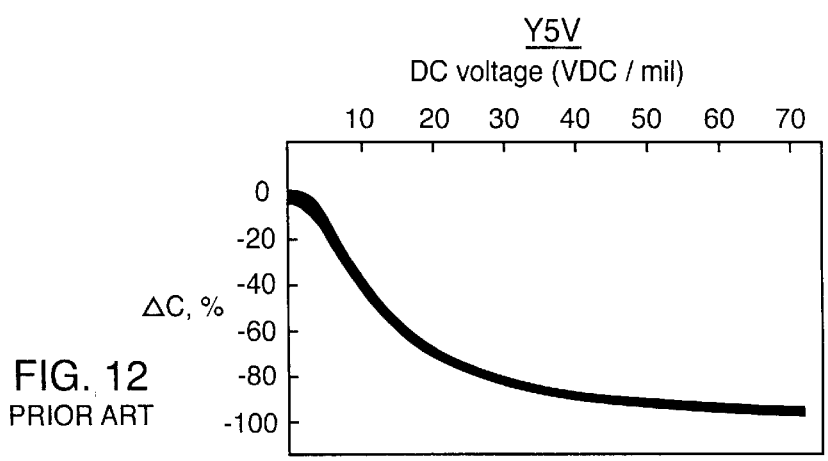
FIG. 12 PRIOR ART

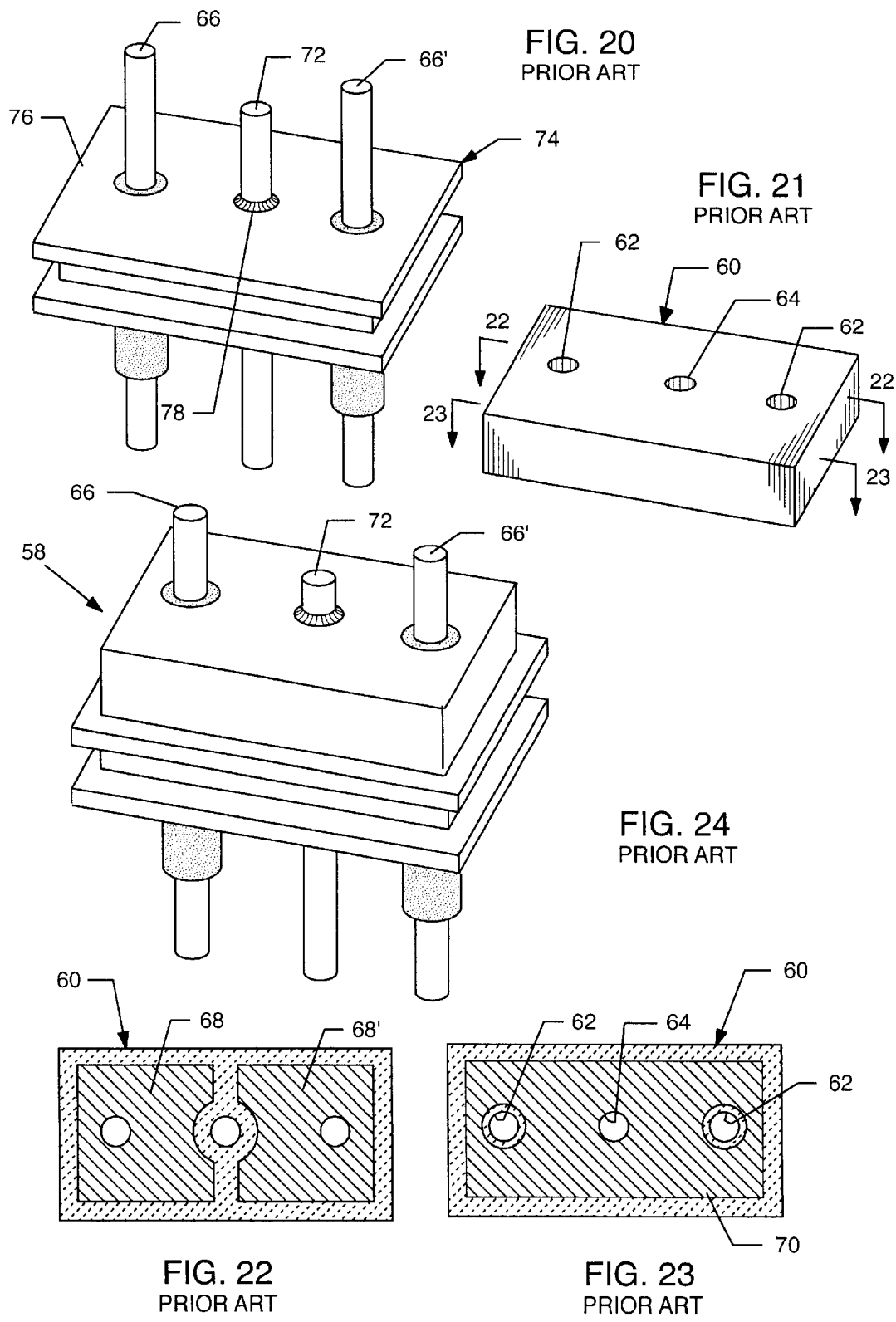

MONOLITHIC CERAMIC CAPACITOR WITH BARIUM TITINATE DIELECTRIC CURIE POINT OPTIMIZED FOR ACTIVE IMPLANTABLE MEDICAL DEVICES OPERATING AT 37° C.

RELATED APPLICATION

This application is a continuation-in-part of U.S. patent application Ser. No. 09/872,092, filed May 31, 2001, which issued as U.S. Pat. No. 6,456,481 on Sep. 24, 2002.

BACKGROUND OF THE INVENTION

This invention relates generally to feedthrough capacitor terminal pin subassemblies and related methods of design and construction, for protecting implantable medical devices from electromagnetic interference commonly found in the environment. More specifically, the present invention relates to improved performance feedthrough capacitor terminal pin subassemblies which offer attenuation to EMI at lower frequencies and also at higher attenuation levels, particularly in medical implant applications.

Feedthrough terminal assemblies are generally well known for connecting electrical signals through the housing or case of an electronic instrument. For example, in an implantable medical device, such as a cardiac pacemaker, defibrillator or the like, the terminal pin assembly comprises of one or more conductive terminal pins supported by an insulator structure for feedthrough passage from the exterior to the interior of the medical device. Many different insulator structures and related mounting methods are known for use in medical devices wherein the insulator structure provides a hermetic seal to prevent entry of body fluids into the housing of the medical device. However, the feedthrough terminal pins are typically connected to one or more lead wires which are connected to cardiac tissue or other tissue to be stimulated which effectively act as an antennae and tend to collect stray electromagnetic interference (EMI) signals for transmission into the interior of the medical device. The hermetic terminal pin subassembly has been combined in various ways with a ceramic feedthrough filter capacitor to decouple interference signals to the housing of the medical device.

Most implantable medical devices in the United States today incorporate feedthrough capacitor EMI filters at their input terminals or in conjunction with the hermetic terminal. However, due to size constraints and mechanical constraints, the capacitance value of these filters has been relatively low (in the 490 to 4000 picofarad range). These capacitance values have been very effective for attenuation of cell phones and other high frequency emitters, however, they do very little to protect the implantable medical device against lower frequency EMI.

It has been well-documented in in-vivo and in-vitro studies that certain kinds of electromagnetic interference can cause disruption of the implantable medical device. For example, in cardiac pacemakers it has been shown that digitally modulated EMI can cause pacemaker inhibition, asynchronous pacing or missed beats. All of these conditions would be highly undesirable and potentially life threatening in a pacer-dependent patient. It has also been shown that EMI can cause an implantable cardioverter defibrillator to inadvertently deliver its high voltage shock therapy. This is very uncomfortable to the patient and is equivalent to a very hard blow to the chest. In prior art devices, such as those shown in U.S. Pat. Nos. 5,333,095; 4,424,551; 5,905,627; 5,751,539 and 6,008,980 (the contents of which are incorporated herein), the hermetic terminal pin subassembly has been combined in various ways with a ceramic feedthrough capacitor filter to decouple and shield electromagnetic interference (EMI) signals into the housing of the medical device.

For example, FIG. 1 is a cut away view of a typical cardiac pacemaker 30 showing an internal circuit board 32 and a broadband EMI filter 34. In order for the broadband EMI filter 34 to work properly, it must be mounted directly at the point of lead 36 ingress and egress.

The broadband EMI filer 34 is typically of coaxial construction also known as a feedthrough capacitor EMI filter. The feedthrough capacitor 34 is optimally bonded directly to the hermetic terminal 38 (FIG. 2) of the implantable medical device that is used to exclude entry of body fluid. The location of the broadband EMI filter 34 at the point of lead ingress and egress is essential so that undesirable incoming EMI signals can be decoupled and shunted directly to the titanium or stainless steel pacer or can or housing 40 and dissipated as harmless energy (heat).

With reference to FIG. 2, in a typical prior art unipolar construction (as described in U.S. Pat. No. 5,333,095), a round/discoidal (or rectangular) ceramic feedthrough filter capacitor 42 is combined with a hermetic terminal pin assembly 38 to suppress and decouple undesired interference or noise transmission along a terminal pin or lead 36. The feedthrough capacitor 42 is coaxial having two sets of electrode plates 44, 46 embedded in spaced relation within an insulative dielectric substrate or base 48, formed typically as a ceramic monolithic structure. The dielectric substrate or base 48 is generally constructed of barium titinate dielectrics that have been built doped with suitable materials to form the desired dielectric properties. One set of the electrode plates 44 is electrically connected at an inner diameter cylindrical surface of the coaxial capacitor structure 42 to the conductive terminal pin 36 utilized to pass the desired electrical signal or signals. The other or second set of electrode plates 46 is coupled at an outer diameter surface of the discoidal capacitor to a cylindrical ferrule 50 of conductive material, wherein the ferrule is electrically connected in turn to the conductive housing 40 of the electronic device 30. The number and dielectric thickness spacing of the electrode plate sets 44, 46 varies in accordance with the capacitance value and the voltage rating of the coaxial capacitor 42. The outer feedthrough capacitor electrode plates 46 (or "ground" plates) are coupled in parallel together by a metallized layer 52 which is either fired, sputtered or plated onto the ceramic capacitor 42. This metallized band, in turn, is coupled to the ferrule 50 by conductive adhesive, soldering, brazing, welding, or the like. The inner feedthrough capacitor electrode plates 44 (or "active" plates) are coupled in parallel together by a metallized layer 54 which is either glass frit fired or plated onto the ceramic capacitor 42. This metallized band 54, in turn, is mechanically and electrically coupled to the lead wire 36 by conductive adhesive or soldering, or the like. In operation, the coaxial capacitor 42 permits passage of relatively low frequency electrical signals along the terminal pin 36, while shielding and decoupling/attenuating undesired interference signals of typically high frequency to the conductive housing 40. Feedthrough capacitors of this general type are available in unipolar (one), bipolar (two), tripolar (three), quadpolar (four), pentapolar (five), hexpolar (6) and additional lead configurations. The feedthrough capacitors (in both discoidal and rectangular configurations) of this general type are commonly employed in implantable cardiac pacemakers and defibrillators and the like, wherein the pacemaker housing 40 is constructed from a biocompatible metal such as titanium alloy, which is electrically and mechanically coupled to the hermetic terminal pin assembly 38 which is in turn electrically coupled to the coaxial feedthrough filter capacitor 42. Alternatively, the feedthrough capacitor can be grounded to one or more terminal pins as described in U.S. Pat. No. 5,905,627. As a result, the filter capacitor 42 and terminal pin assembly 38 prevents entrance of high frequency interference signals to the interior of the pacemaker housing 40, wherein such interference signals could otherwise adversely affect the desired cardiac pacing or defibrillation function.

Feedthrough filter capacitors for cardiac pacemakers and the like, have typically been constructed by preassembly of the coaxial capacitor 42 onto or within a cylindrical or rectangular hermetically sealed terminal pin subassembly 38 which includes the conductive pin 36 and ferrule 50. More specifically, the terminal pin subassembly 38 is prefabricated to include one or more conductive terminal pins supported within the conductive ferrule by means of a hermetically sealed insulator ring or bead 56. One type of hermetic terminal pin subassembly 38 which is widely used in implantable medical devices employs an alumina ceramic insulator 56 which is gold brazed into a titanium ferrule 50. In addition, the platinum lead wire 36 is also gold brazed to the alumina ceramic insulator 56 to complete the hermetic seal. See for example, the subassemblies disclosed in U.S. Pat. Nos. 3,920,888; 4,152,540; 4,421,947; and 4,424,551. An improved design in the prior art which has substantially improved the volumetric efficiency is based upon surface mounting of a ceramic feedthrough capacitor planar array structure to one outer surface of a hermetic terminal with similar connection to the conductive pins (see the subassemblies disclosed in U.S. Pat. No. 5,333,095).

Prior art feedthrough capacitors used as EMI filters in implantable medical devices have all been limited in capacitance value. This is due to the extreme constraints put on volume, size and weight in active implantable medical devices. Major trends affecting the implantable medical electronics industry are the following factors:

1. Reduction in size.
2. Reduction in weight.
3. Increase in longevity or battery life.
4. Increase in number of functions.
5. Reduction in cost.
6. Increase in performance.

Prior art feedthrough capacitors have generally used commercial (EIA Designations) dielectrics designated by BX, X7R or NPO types. These are barium titinate dielectrics that grew out of use in military, space applications and other mission critical applications.

The Electronics Industry Association (EIA) has developed a number of codes for capacitors known as EIA Standard RS198. Included in this standard are a number of descriptive letter codes (Z5U, Y5V, X7R, etc.) that designate how much the capacitance of a capacitor will change over various temperature ranges. The first letter signifies the low operating temperature. The second letter indicates the maximum amount the capacitance will change. The number between gives the high operating temperature. FIG. 3 gives a few examples of how this code works. In particular, FIG. 3 illustrates prior art EIA temperature characteristic codes that are commonly used in monolithic ceramic capacitor industry. This explains how the codes work. We will use an X7R capacitor as an example. The letter X designates the low temperature operating point which you can see from the Table is −55° C. The "7" illustrates the high temperature operating point which is 125° C. The "R" designates the maximum allowable capacitance change between these two temperature extremes, which in this case is +/−15%. As a second example, we could consider Y5V. "Y" would indicate that the low temperature operating point is −30° C. "5" indicates the high temperature operation point is 85° C. The "V" indicates that the capacitance can change in value over that full range any where from +22% to −82% (a total chnage in capacitance of 104%).

These dielectrics are generally formulated starting with pure barium titinate, which inherently has a very high dielectric constant (K). Unfortunately, pure barium titinate also is very unstable in terms of temperature and voltage. Most titinates (for instance, barium titinate) undergo crystalline inversions which result in very high values of dielectric constant near the temperature at which the shift occurs (the Curie point). In the case of barium titinate, the Curie temperature is about 120° C. At temperatures above the Curie temperature, titinates are not ferro-electric (they are paraelectric). At temperatures below the Curie temperature, they are ferro-electric and can be used in piezoelectric applications. The alkaline earth titinates (calcium, strontium, magnesium and barium) are the basic materials used in making monolithic ceramic capacitors. The most commonly used is barium titinate. As previously mentioned, it has a Curie point at about 120° C.

FIG. 4 illustrates the change in dielectric constant (or K) with temperature between 25° C. and 120° C. of pure barium titinate. Materials can be added to the high K barium titinate ceramic to depress the Curie peak, resulting in a formulation that has less temperature dependency. One of the trade-offs is that this tends to lower the dielectric constant. Increasing the amount of depressor decreases the amount of temperature variability. FIG. 5 illustrates a prior art technique of using a depressor to depress the Curie point peak. This has the effect of making the dielectric constant of the capacitor much more stable over the operating temperature range. Materials used to depress the Curie peak usually stay in the grain boundary of the polycrystalline ceramic as opposed to Curie shifters which enter into the crystalline structure itself. As previously shown in FIG. 4, unmodified barium titinate has a very high dielectric constant at its Curie temperature, which drops to relatively low values at a low temperature, such as room temperature at 25° C. This relates directly to the volumetric efficiency of the finished capacitor. For example, a capacitor built from pure barium titinate would have a dielectric constant of roughly 1800 at 25° C., but over 22,000 at 120° C. This capacitor would have tremendous volumetric efficiency if operated at only 120° C. Referring now again to FIG. 5, depressors are added generally into the grain boundary of the polycrystalline ceramic. This is different from Curie point shifters, which generally enter into the crystalline structure itself. Depressors mean that the capacitor will be made more stable over temperature. However, the trade off is the sacrifice of dielectric constant. In the extreme case, the dielectric constant can be depressed all the way down to below 100 and that means that its variation in dielectric constant and also capacitance will be less than 0.5% when the device is exercised over the temperature range −55 to +125° C.

Curie point shifters are materials which can be added to barium titinate that will shift the Curie temperature to another temperature. For example, lead titinate is one material that will move the Curie temperature up. Strontium titinate is an example of a material that will shift it downward. Shifters enter into solid-state solution with the barium titinate. The resulting misfit in the crystal lattice causes energy changes which makes the crystalline inversion occur at a different temperature. FIG. 6 illustrates the concept of using prior art Curie point shifters. Shifters are materials that are added to the barium titinate that will shift the Curie temperature to another temperature. Lead titinate will generally move the Curie temperature up. Strontium titinate and other materials are examples of materials that will shift it downward.

Shifters enter into solid-state solution with the barium titinate. A resulting misfit in the crystal lattice causes energy changes which makes the crystalline inversion occur at a different temperature. FIG. 6 illustrates curve 1 which is pure barium titinate with an inherent Curie point of roughly 120° C. Curve 2 indicates just enough shifter to shift the Curie point to 37° C., which is body temperature. This has not been done before in a standard commercial dielectric, but would optimize the device for operation only at 37° C. (body temperature). Curve 3 illustrates a curve with the addition of more shifter which would cause the Curie peak to occur at roughly room temperature (20°–25° C.). There are a set of commercial dielectrics that are commonly available that are represented by FIG. 3, including Y5V and other commercially available dielectrics.

In the past, such unstable dielectric materials such as Y5V have not been used for human implant applications because they are generally considered unreliable and are too temperature unstable (at 37 degrees C. there is still about a 20 to 40 percent drop in capacitance compared to operation right at the 20 to 25° C. Curie peak of Y5V). For general military and space applications, ceramic dielectrics have been formulated which are very temperature stable over the full operating military and space temperature ranges from −55° to +125° C. Accordingly, the inherent dielectric constant of barium titinate, which can run as high as 22,000, has been depressed into the range of approximately 2500 or even lower. Volumetric efficiency is sacrificed for this depression of Curie point; however, the change in capacitance with temperature can be held to very tightly controlled limits. For example, in the case of BX and X7R, the maximum allowable temperature change is +/−15% over the operating temperature range from −55 to +55° C., which is acceptable for most military, space and other mission critical applications.

Another very important aspect to consider with ceramic dielectrics is voltage stability. When DC bias voltage is applied to a monolithic ceramic capacitor, the amount of capacitance value drops. The amount of drop is related to the volts/mil stress on the ceramic dielectric and also the dielectric constant itself. The volts/mil stress is simply found by taking the dielectric thickness between the electrodes of the capacitor and dividing that thickness into the applied voltage. For example, a capacitor with a 100 volts applied to it that has 2 mils of fired dielectric thickness would have an applied stress of 50 volts/mil. When 50 volts/mil is applied to a ceramic BX dielectric with a dielectric constant of around 1500 (this means the Curie point has been significantly depressed) the capacitance will drop approximately 10% in value as illustrated in FIG. 7. A drop of 10% is generally acceptable in military, space and related applications. Also, by doubling the dielectric thickness, the stress becomes 25 volts/mil which one can see from FIG. 7 only causes a drop of approximately 3.5% in capacitance (and even more drop in volumetric efficiency).

More specifically, FIG. 7 illustrates the propensity of a prior art 1500K and BX monolithic ceramic capacitor to drop slightly in capacitance with applied DC bias voltage. What this means is that the dielectric stress between opposed electrodes causes the crystal lattice to drop in K. The way one interprets FIG. 7 would be best illustrated by an example: Let's assume that we have designed a capacitor with a dielectric thickness of 2 mils after all manufacturing operations including sintering. If one were to apply 100 volts DC bias to this capacitor, one could readily calculate the DC voltage stress in volts/mil. We would simply take the 100 volts applied and divide it by 2 mils which would yield a stress on the dielectric of 50 volts/mil. As one can see, at 50 volts/mil the capacitance is down approximately 10%. This is typical of a commercial designation BX dielectric, which in general has a K of roughly 1500 to 2800. This device has been quite popular in the prior art and is used in many high reliability applications in military, space and medical applications.

FIG. 8 illustrates the temperature coefficient (TC) curve of the same dielectric as described in FIG. 7. In this case, it has an inherent dielectric constant of 1500. This illustrates the change in capacitance with temperature. As can be seen, this is a relatively stable dielectric with a Curie point of approximately 120° C. At −55° C., the capacitance drops about 9% and at +125° C., the capacitance drops approximately 7%. This is a very stable dielectric suitable for use in military and space applications. The negative trade-off is that it is not very volumetrically efficient.

The foregoing discussion relates to representative examples of typical dielectrics found in the prior art. These curves were published by Solid State Dielectrics, Inc., which initially formulated these materials. FIG. 8 illustrates the change in capacitance with temperature of the 1500 K dielectric previously described. As one raises the dielectric constant, the capacitor becomes more volumetrically efficient. However, both the temperature stability and voltage stability of the capacitor are severely affected. FIG. 9 illustrates the temperature stability of a common commercial dielectric known as Z5U. It has a dielectric constant of around 7000 and has a much greater change in capacitance over temperature stability. As one can see, the operating temperature range is narrowed. For a typical military-type capacitor, the operating temperature range would be specified for −55 to +125° C. However, the Z5U dielectric is only rated to operate between −25 and +85° C. Over this restricted operating temperature range, the capacitance drops as much as 50% in capacitance from its initial room temperature value.

The application of DC voltage also greatly affects this higher K dielectric. FIG. 10 illustrates the change in capacitance with applied DC voltage in volts/mil. Assuming the same example that we previously described for the BX dielectric, as one can see, at 50 volts/mil, this dielectric drops almost 80% in capacitance. It also should be noted that the capacitance change and temperature change effects are accumulative. That is if this capacitor was operated at 125° C. with 50 volts/ml bias, one would only have a few percent of the initial capacitance left. This is one reason why this particular grade of capacitor dielectric is generally not used in high reliability/mission critical applications. It is a common component in consumer electronics, such as car stereos and the like, which are generally only expected to operate at low voltage and near room temperature.

The effects of voltage bias and temperature are cumulative. For example, if one were to take this Z5U commercial dielectric and cool it down to −25° C. while at the same time applying 50 volts/mil, almost all of the capacitance would be gone.

Another prior art commercial dielectric is known as Y5V. It has a dielectric constant above 12,000 and is very volumetrically efficient for room temperature applications. FIG. 11 illustrates the change in capacitance with temperature, which is even more severe than the previously described Z5U. For example, at −25° C., this particular dielectric loses 80% of its capacitance. The higher the dielectric constant is raised, the more unstable the capacitor becomes both with applied temperature and applied DC bias. At −25° C., the capacitance drops approximately 80% and at +85° C., the capacitance drops about 82%.

Y5V is also remarkably unstable in the presence of applied DC voltage. FIG. 12 represents the prior art Y5V capacitor's drop in capacitance with applied DC bias. Using the same example of a capacitor of 2 mils of fired dielectric thickness and 100 volts DC applied, one has a dielectric stress of 50 volts/mil. At this 50 volts/mil stress level from the FIGURE, one can see that there is an approximate 90% drop in capacitance. This normally would be highly undesirable in an EMI filter because greatly reduced attenuation would result. While the use of this commercial dielectric might be contemplated at 37 degrees (human implant temperature), as one can see from FIG. 11, the capacitance value will drop almost 40 degrees C. as compared to the Curie peak which is between 20 and 25 degrees C.

As one increases the dielectric constant, one also gives up a number of other design parameters in addition to temperature stability and voltage sensitivity. One of these is dielectric breakdown strength. In general, as one increases the dielectric constant of the capacitor, the dielectric breakdown strength measured in volts/mil declines. FIG. 13 generally illustrates this effect showing that as one increases the dielectric constant to above 10,000, the dielectric breakdown strength declines significantly. Specifically, FIG. 13 represents prior art ceramic dielectrics. The X-axis shows the dielectric constant and the Y-axis indicates the dielectric breakdown strength between the electrode plates measured in volts DC/mil. As one can see, in general, dielectric strength tends to drop the higher the dielectric constant. For example, low K dielectrics (less than 100 K) generally have dielectric breakdown strengths of over 1000 volts/mil. However, high K commercial dielectrics (that are in the range of 7000 or higher) generally have dielectric breakdown strengths just slightly above 400 volts/mil. It should be noted that as you increase the K, mechanical strength is also sacrificed.

Ferro-electric materials exhibit a number of special properties, including dielectric historisis. Ferro-electric materials are also piezoelectric, in that they have capabilities of converting mechanical movement or pressure to electrical signals or energy and visa versa. Barium titinate is generally known as a ferro-electric material when operating below its Curie point. The capacitor's ferro electric or piezoelectric behavior is a major design consideration for EMI feedthrough capacitors used in the output of implantable cardioverter defibrillators. When a high voltage pulse is applied to the EMI filter, significant mechanical stresses are generated. One of the reasons for the great commercial success of U.S. Pat. Nos. 5,333,095 and 5,905,627 is that these designs allow the ceramic capacitor to expand and contract during the application of the high voltage pulse. In this way, the piezoelectric stresses are well managed.

Another important design property that one sacrifices as the dielectric constant increases is mechanical strength. High K dielectrics simply are not as mechanically strong both in terms of tensile, compression or breaking strength as compared to lower K dielectrics. In addition, they exhibit a much lower modulus of toughness. It is a general principle of ceramic engineering that low K dielectrics are mechanically very robust. An example of this is the alumina ($AL_2O_3$) insulator used in the hermetic insulators of implantable medical devices. Alumina insulators have excellent mechanical properties including a very high modulus of toughness and high tensile and compressive strength. Accordingly, they make for very robust hermetic seals through which lead wires pass. They can withstand the heat of laser welding and also handling by operators during the manufacturing and installation of the device. Alumina ($Al_2O_3$) ceramic, however, has a very low dielectric constant (less than 7) and could not be used to make a feedthrough capacitor due to the very poor volumetric efficiency that would result.

For the reasons described above, extremely high K dielectrics (above K=7000) have not been used extensively in high reliability and/or high performance military and space applications. In military and space applications, where temperature stability and voltage stability are critical, such materials are contraindicated. High K dielectrics such as Y5V and Z5U do find commercial applications in consumer electronics, computers and the like. The reason for this is that such devices are not exposed to extremes in temperature conditions and the voltage applied to the capacitors can be managed to be very stable. There is no known application where a high K dielectric (above 7000) has been used for the feedthrough capacitor EMI filter of an implantable medical device.

High K dielectrics have also been contraindicated in mission critical applications due to the general impression in the industry that they are unreliable. By unreliable, it is meant prone to failure, either due to degradation of insulation resistance, or outright electrical short (catastrophic failure).

Accordingly, there is a need for a highly reliable monolithic ceramic feedthrough capacitor which is utilized in combination with the hermetic seals of active implantable medical devices such as cardiac pacemakers, implantable cardioverter defibrillators (ICDs), cochlear implants and the like, wherein the feedthrough capacitor dielectric material comprises a very high dielectric constant material whose Curie point has been shifted to approximately 37 degrees C. with very little or no Curie peak depressor. Such a feedthrough capacitor would advantageously push the effective K available to above 7000 and allow EMI feedthrough capacitors for implantable medical devices to be built in the same physical size or smaller with much higher capacitance values. The present invention fulfills these needs and provides other related advantages.

SUMMARY OF THE INVENTION

The present invention describes monolithic ceramic feedthrough capacitors used in combination with the hermetic seals of active implantable medical devices such as cardiac pacemakers, implantable cardioverter defibrillators (ICDs), cochlear implants, neurostimulators, and the like. The feedthrough capacitor dielectric is a novel very high dielectric constant material whose Curie point has been shifted to approximately 37 degrees C. with very little to no Curie peak depressor. This pushes the effective K available to above 7000 (up to a maximum of approximately 22,000). This allows EMI feedthrough capacitors for implantable medical devices to be built in the same physical size (or even smaller) with much higher capacitance values. The higher capacitance provides additional attenuation to EMI caused by emitters in the frequency range from the high kilohertz all the way up to several gigahertz.

The present invention embraces a dielectric technology wherein the capacitance value of the EMI filter can be raised to much higher levels therefore providing immunity to EMI over a much broader frequency range.

A particular feature of the present invention is a unique property of the high dielectric constant material to decrease in capacitance with applied voltage. This is of particular advantage in output of an implantable cardioverter defibrillator (ICD). Excessive capacitance on the output leads of the ICD can degrade the pulse and also affect its energy efficiency. It is a property of high K dielectric capacitors that they drop drastically in capacitance value during the application of high voltage thereby preventing this problem. During the quiescent period, in other words, when the implantable defibrillator is not providing high voltage shock therapy, the full capacitance value is available to protect against electromagnetic interference. This is important as most EMI problems occur when the implantable device is in the cardiac signal sensing mode and detecting signals form hundreds of microvolts to several millivolts.

More particularly, the present invention relates to a novel process for manufacturing a monolithic ceramic capacitor for use in an active implantable medical device. The process steps include providing a dielectric material having a dielectric constant greater than 7000, adding one or more Curie point shifters to the dielectric material to optimize the monolithic ceramic capacitor dielectric constant at the human body temperature of 37° C., and processing the dielectric material with one or more shifters into a finished capacitor having first and second sets of electrode plates disposed therein. In the preferred embodiment, a dopant may be used to broaden the Curie point peak of the dielectric material, and the monolithic ceramic capacitor is typically configured as a feedthrough filter capacitor designed for incorporation into an EMI filter. Such a filter is useful when installed in a high voltage defibrillator circuit of an implantable medical device. The dielectric material is further optimized so that during the delivery of high-voltage electrical energy, such as a bi-phasic or mono-phasic fast rise time defibrillation pulse, the capacitance value of the capacitor drops to less than 65% of its initial value, and preferably less than 20% of its initial value.

In a feedthrough filter capacitor assembly for use in an active implantable medical device, the invention comprises at least one conductive terminal pin, the novel feedthrough filter capacitor of the present invention, and a conductive ferrule through which the terminal pin passes in nonconductive relation. The feedthrough filter capacitor has first and second sets of electrode plates disposed within a dielectric material having a dielectric constant greater than 7000, and a first passageway through which the terminal pin extends in conductive relation with the first set of electrode plates. The feedthrough filter capacitor is optimized for operation within the temperature range of 30° C. to 40° C., and preferably at 37° C. In a preferred embodiment, the dielectric constant of the dielectric material is within the range of 8500 to 22,000. The dielectric material includes at least one dopant used to shift the Curie point to 37° C. It is often necessary to include a Curie point depressor for broadening the temperature bandwidth of the Curie point peak or point of maximum dielectric constant. Typical dopants utilized include strontium titinate, lead titinate, zirconium dioxide, barium carbonate, zinc oxide, zinc borate, manganese carbonate, and titanium dioxide. Typical applications include cardiac pacemakers, ICD's, hearing implants, congestive heart failure treatment devices, atrial defibrillators, bi-ventricular pacemakers, neurostimulators, brain stimulators, bladder control stimulators, artificial eyes, artificial noses, RF muscle actuators, implanted limb manipulation systems, artificial hearts and ventricular assist devices.

The present invention is further particularly useful in feedthrough filter capacitor assemblies for use in human implant applications utilizing an internal ground configuration. There the assembly includes at least one conductive terminal pin, a conductive ferrule through which the terminal pin passes in non-conductive relation, the novel feedthrough filter capacitor of the present invention, and a ground lead which extends into a second passageway through the feedthrough filter capacitor, wherein the ground lead is conductively coupled to the second set of electrode plates and the conductive ferrule.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 3 is a chart of EIA temperature characteristic codes;

FIG. 4 is a graph illustrating the change in dielectric constant with temperature between 25 degrees C. and 120 degrees C. of pure barium titinate;

FIG. 5 is a graph illustrating a prior art technique of using a depressor to depress the Curie point peak;

FIG. 10 is a graph illustrating the change in capacitance with applied DC voltage in volts/mil for a ceramic Z5U dielectric;

FIG. 11 is a graph illustrating the change in capacitance with temperature for a ceramic Y5V dielectric;

FIG. 12 is a graph illustrating the Y5V capacitors drop in capacitance with applied DC bias;

FIG. 20 is a perspective view of a prior art internally grounded hermetic terminal with two bipolar leads;

FIG. 21 is a perspective view of a prior art internally grounded rectangular ceramic feedthrough capacitor;

FIG. 22 is a sectional view taken generally along the line 22—22 illustrating the configuration of active electrode plates within the capacitor;

FIG. 23 is a sectional view taken generally along the line 23—23 of FIG. 21, illustrating the configuration of ground electrode plates within the capacitor;

FIG. 24 is a perspective view of a prior art EMI filter comprising the hermetic terminal and capacitor of FIGS. 20 and 21 assembled to one another;

DETAILED DESCRIPTION OF THE PREFERRED EMBODIMENTS

In accordance with the present invention, the use of very high K dielectric materials which are above K=7000 and optimized for 37° C. operation, allows for significantly more capacitance per unit volume. This is particularly important in the next generation of implantable EMI feedthrough filters, which now must provide effective attenuation at lower frequencies. This is due to the increasing EMI threat of electronic article surveillance systems (EAS) or retail store's security systems, security scanners, such as hand held airport wands, 10 MHz RFID systems, and the 27 MHz and 70 to 76 MHz popular operations bands for model airplanes, helicopters, boats and the like. Many engineers have previously thought that an undesirable property of extremely high K barium titinate dielectrics is that their K and capacitance will drop dramatically in the presence of DC bias voltages measured in volts/mil of dielectric thickness. However, this is not a problem at all in pacemakers, cochlear implants and neurostimulators where the therapeutic impulses are very low in magnitude (in the range of only a few volts). The large drop in capacitance of a high voltage implantable cardioverter defibrillator application actually turns out to be an advantage. Having the capacitance of an EMI filter drop during the ICD pulse is desirable as there is less capacitive loading of the circuit during pulse discharge, less energy loss, and less capacitor electrode plate charging current. When the ICD is passive (monitoring cardiac electrical activity), the capacitance of the EMI filter would be desirably high, which is exactly the time when EMI is a concern. It has been well documented that an ICD can interpret electromagnetic interference as a fast heart rate and confuse it with ventricular tachycardia or ventricular fibrillation and thereby cause it to deliver an inappropriate and very painful high voltage shock when the patient does not need one.

When used in combination with a low stress capacitor mounting techniques, particularly those described in U.S. Pat. Nos. 5,333,095 and 5,905,627, very low mechanical or thermal stress is placed on the monolithic ceramic feedthrough capacitor. Therefore a preferred embodiment of the present invention is the use of the high K dielectric material in combination with the internally grounded feedthrough filter capacitor of U.S. Pat. No. 5,905,627, or of the feedthrough filter capacitor assembly for human implant of U.S. Pat. No. 5,333,095. In contrast, it would not be feasible to use a structurally weak high K dielectric in a capacitor as described in U.S. Pat. Nos. 4,424,551 or 4,152,540.

Figures 14, 15:
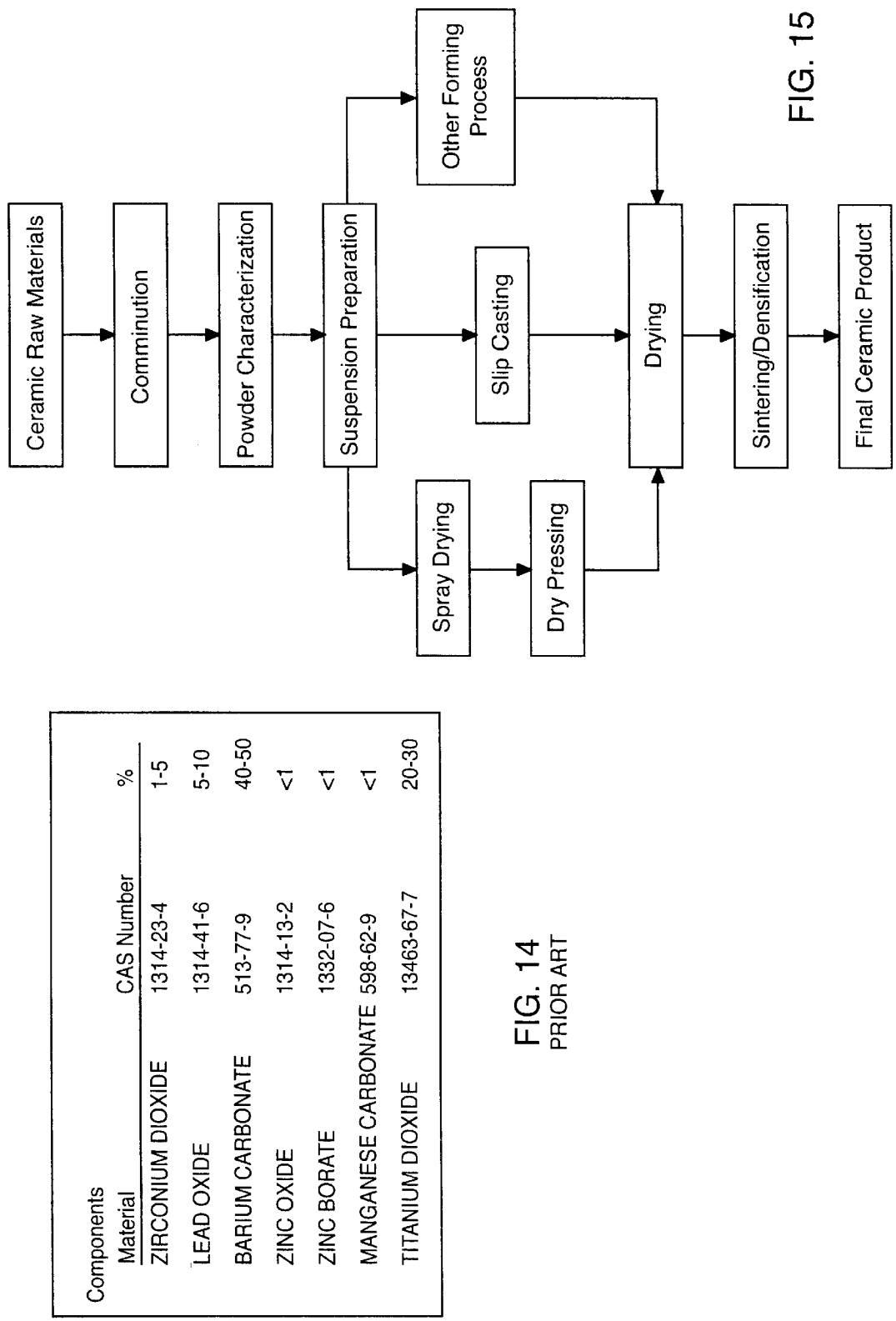
FIG. 14 is a table illustrating the components of Ferro Electronics Materials Company product XL 103/product ID 5881.
FIG. 15 is a flow chart illustrating the process for manufacturing ceramic dielectric material.

In recent years, a number of high K dielectrics have been formulated which are highly reliable and have good insulation resistance and breakdown strength properties. One such example of this is Ferro ZL9000 material, which is a low fire Z5U dielectric. Another example is Ferro XL 103 which is a Z5U dielectric whose materials are listed as FIG. 14. The Table in FIG. 14 is taken from Ferro Electronics Materials' Company Product XL 103/Product ID 58881. This is a high K dielectric with a Curie point close to 20° C. As one can see, it employs zirconium dioxide between 1 and 5%, lead oxide between 5 and 1-%, and so on. It is a novel aspect of the present invention that the dopants, including zirconium dioxide, lead oxide, zinc oxide, zinc borate and manganese carbonate, will be varied in order to shift the Curie point to 37° C. (body temperature). Another example is the Ferro Tamtron XL103, which has a dielectric constant of about 10,000. Ferro also manufactures a dielectric material known as Tamtron Y5V173L, which has a typical dielectric constant of around 18,000. In general, these high K commercially available dielectrics have Curie peaks or maximum K that are near room temperature (25° C.).

By adjusting the dopants and the firing conditions, it is possible to rotate the Curie point or point of maximum dielectric constant to optimize it for human implant application at 37° C. Even without such rotations, these commercially available dielectrics still offer a very high dielectric constant when operated slightly off of the Curie temperature (at 37° C. body temperature).

FIG. 15 illustrates a complete process flow diagram for ceramic raw materials through final ceramic product. As previously noted, one such embodiment of the present invention would involve ceramic raw materials employing 20–30% titanium dioxide, 40–50% barium carbonate, approximately 1.5% zirconium dioxide, approximately 8.2% lead oxide and less than 1% each of zinc oxide, zinc borate and manganese carbonate with other trace elements present. As one can see, the second from the last step in the ceramic capacitor process involves sintering/densification. This is where the capacitor is changed from a grain state into a hard fired monolithic structure. The firing profile can also affect Curie point and final process adjustments can be made at this point to make sure that the Curie point comes out to be 37° C. Sufficient Strontium titinate dopant (or equivalent dopants well known to those in the art) are uniquely added to the ceramic raw material to rotate the Curie point to approximately 37 degrees C. By shifting the Curie point to 37° C. and using very low depressor, the inherent dielectric constant can be as high as 15,000–20,000. This means that the volumetric efficiency of the ceramic capacitor can go up approximately a factor of 6 or even higher.

Figure 16:
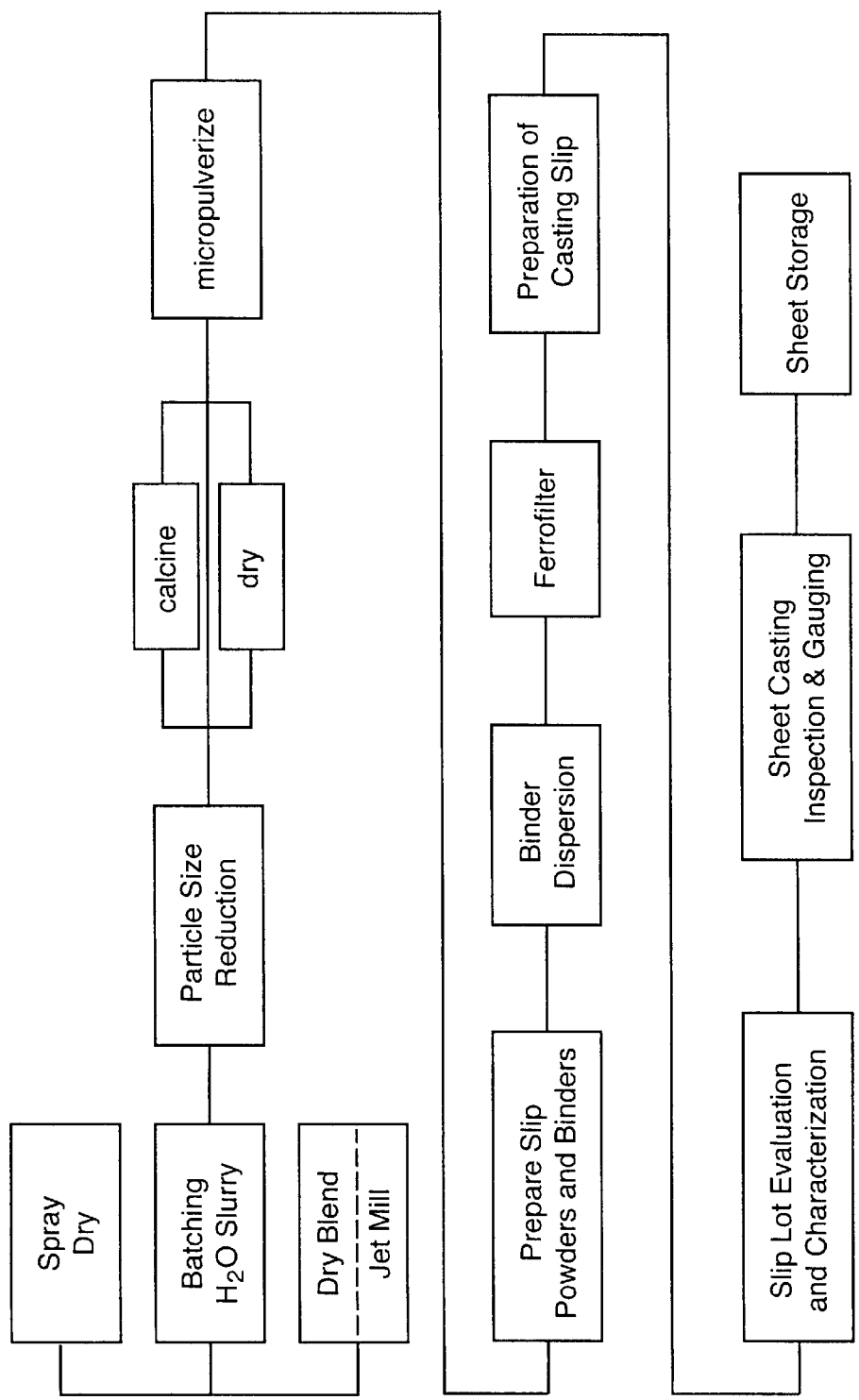
FIG. 16 is a block diagram illustrating various methods to process 37 degrees C. dielectric of the present invention.

FIG. 16 illustrates alternative processing for preparation of ceramic powder all the way through slip casting and sheet storage. FIG. 16 is a block diagram illustrating the various ways to process the 37° C. dielectric of the present invention. The first step has a number of options including the possibility of spray drawing, batching $H_2O$ slurry, dry blending or jet milling. The powder is then taken through a particle size reduction and then followed by calcining and/or drying and then followed by a micropulverizing process (another method involves co-precipitation of the elements). Preparation of slip powders and binders then follows, followed by binder dispersion. During this process, the various components of the dielectric are carefully adjusted in order to shift the Curie peak or point of maximum K from the commonly commercially available dielectrics to a novel use specifically for human implant applications. That is, during this process the point of maximum K will be carefully designed to be at 37° C. This generally occurs during the first three basic blocks in the overall production flow diagram as illustrated.

It is a novel feature of the present invention to use such commercially available high K dielectrics and the like in combination with a human implantable feedthrough capacitor EMI filter. A preferred embodiment of the present invention would be to rotate the Curie point by adjusting the dopants and/or firing conditions so that the Curie point occurs exactly at 37° C. or body temperature. This would optimize the dielectric constant.

Figure 17:
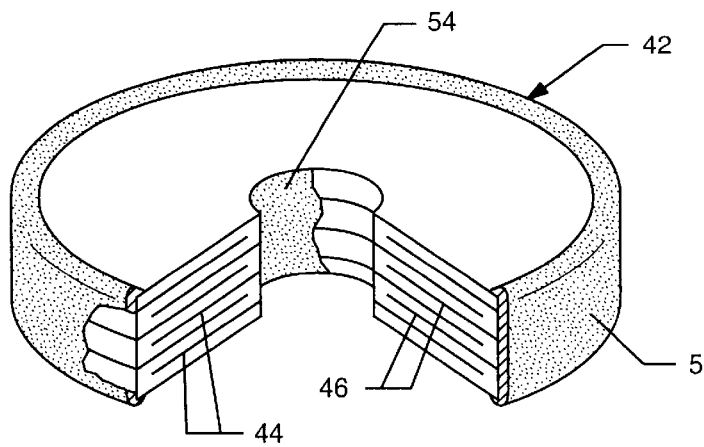
FIG. 17 is a partially fragmented perspective view of the unipolar ceramic feedthrough capacitor of FIG. 2.

FIG. 17 illustrates a unipolar capacitor 42 of the prior art constructed from dielectric material with a dielectric constant of approximately 2500. The capacitor of FIG. 17 has a capacitance value of 2200 picofarads and a voltage rating of 50 volts DC.

Figure 18:
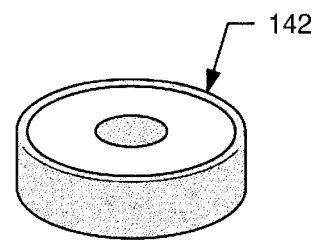
FIG. 18 is a perspective view similar to FIG. 17 of a unipolar ceramic feedthrough capacitor having the same capacitance value, and voltage capability of the capacitor of FIG. 17, but manufactured in accordance with the processes and techniques of the present invention.

FIG. 18 represents the same capacitor 142 using the high K dielectric material of the present invention. This means that it has the same capacitance value, the same voltage capability, but it is much smaller. This would be made from the novel 37° C. Curie point dielectric of the present invention.

The capacitor has been dramatically reduced in size (typically, 4 to 6 times smaller). The capacitor can also be much higher in value (over 10,000 picofarads and/or have a much higher voltage rating. This is all due to the tremendous increase in volumetric efficiency due to the use of a dielectric with a K over 7000 (in this particular example, the K is 18,000).

Figure 1:
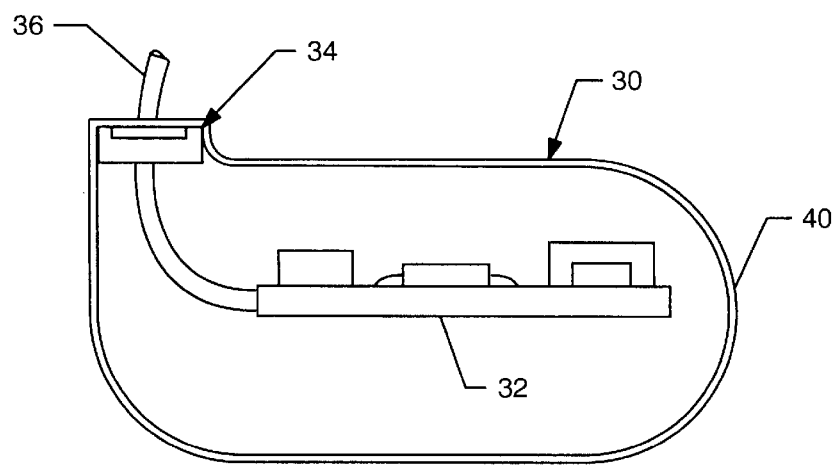
FIG. 1 is a schematic view of a typical cardiac pacemaker.
Figure 2:
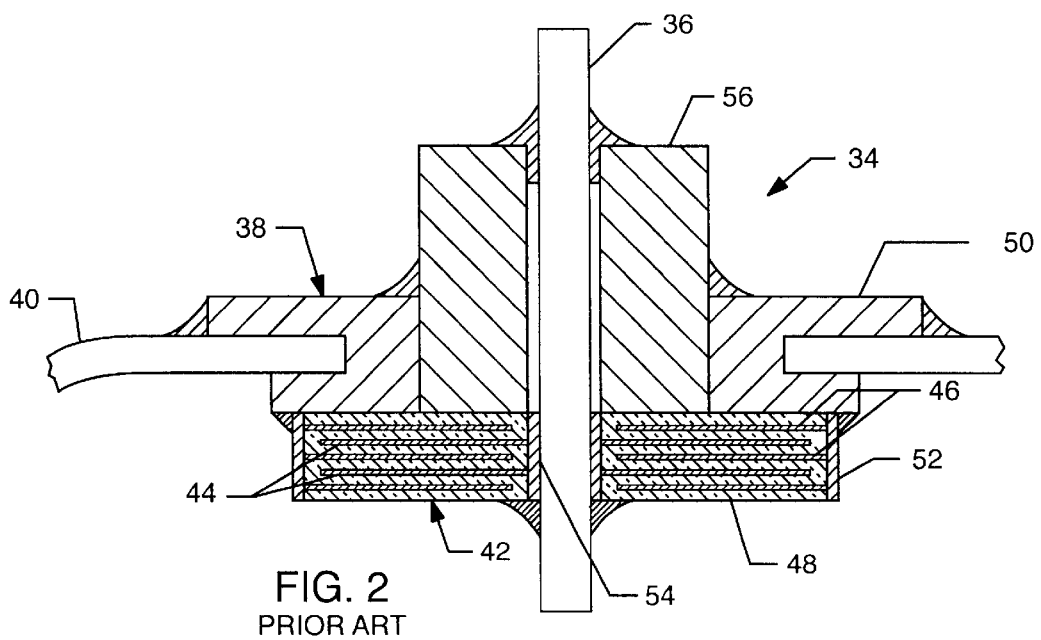
FIG. 2 is an enlarged, fragmented and sectional view of a unipolar feedthrough filter assembly, typical of such assemblies as used in connection with the cardiac pacemaker of FIG. 1.
Figure 6:
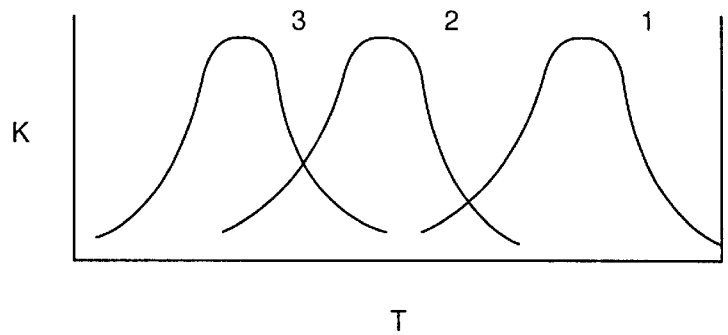
FIG. 6 is a graph illustrating the concept of using Curie point shifters in barium titinate that shift the Curie temperature.
Figure 7:
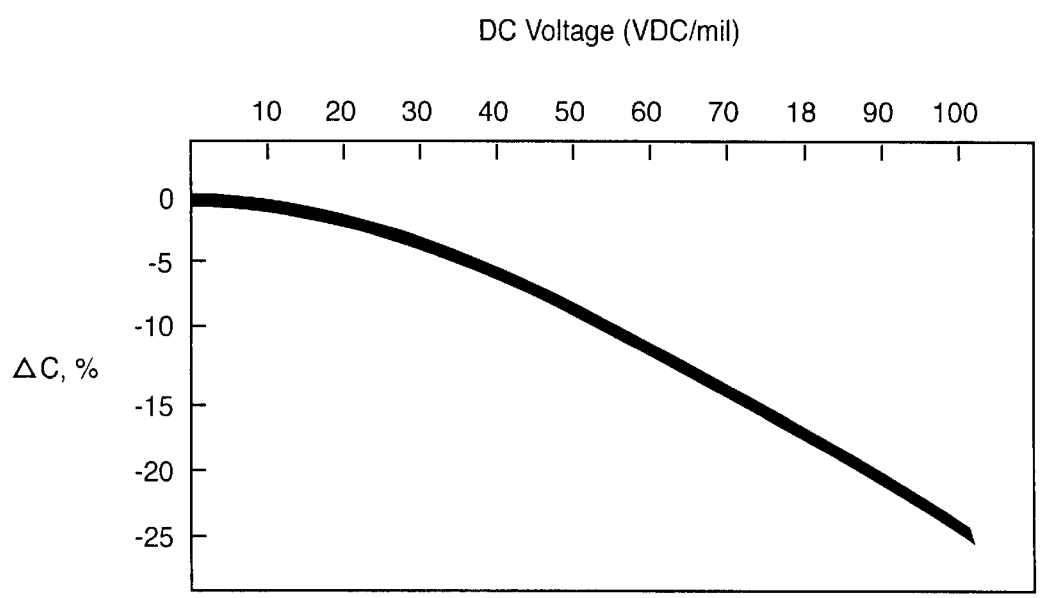
FIG. 7 is a graph illustrating the capacitance change with temperature for a ceramic BX dielectric.
Figure 8:
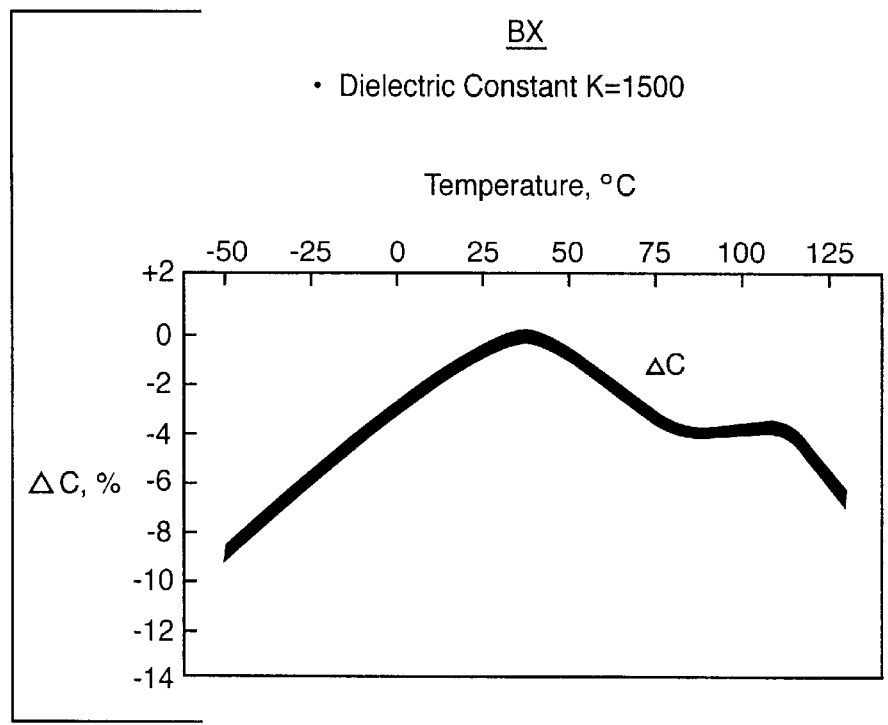
FIG. 8 is a graph illustrating the change in capacitance with temperature of a 1500 K dielectric material.
Figure 9:
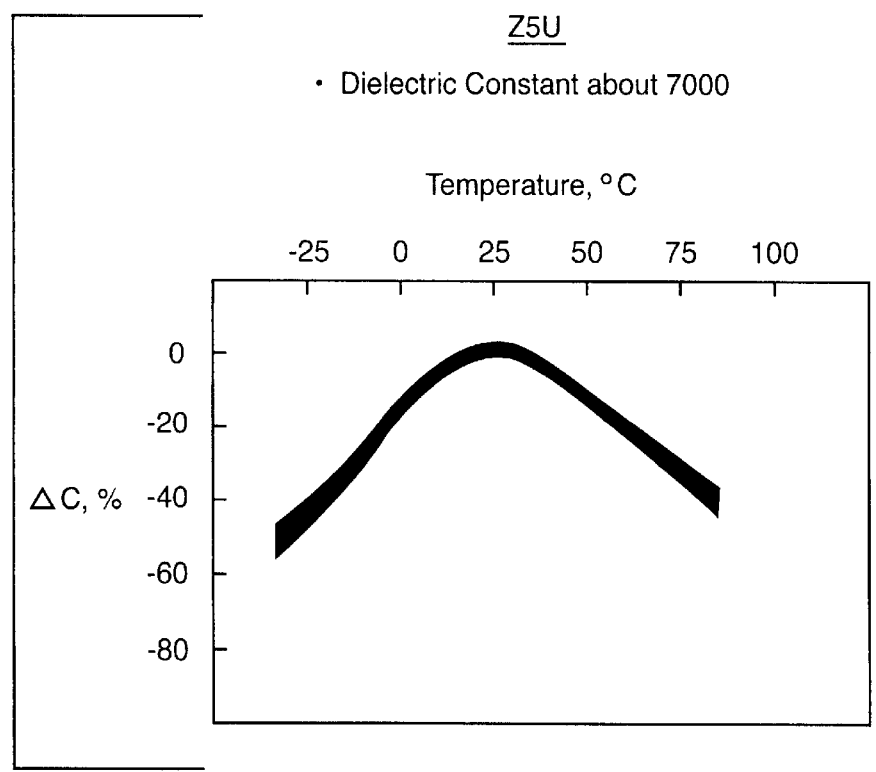
FIG. 9 is a graph illustrating the temperature stability of a common commercial dielectric known as Z5U.
Figure 13:
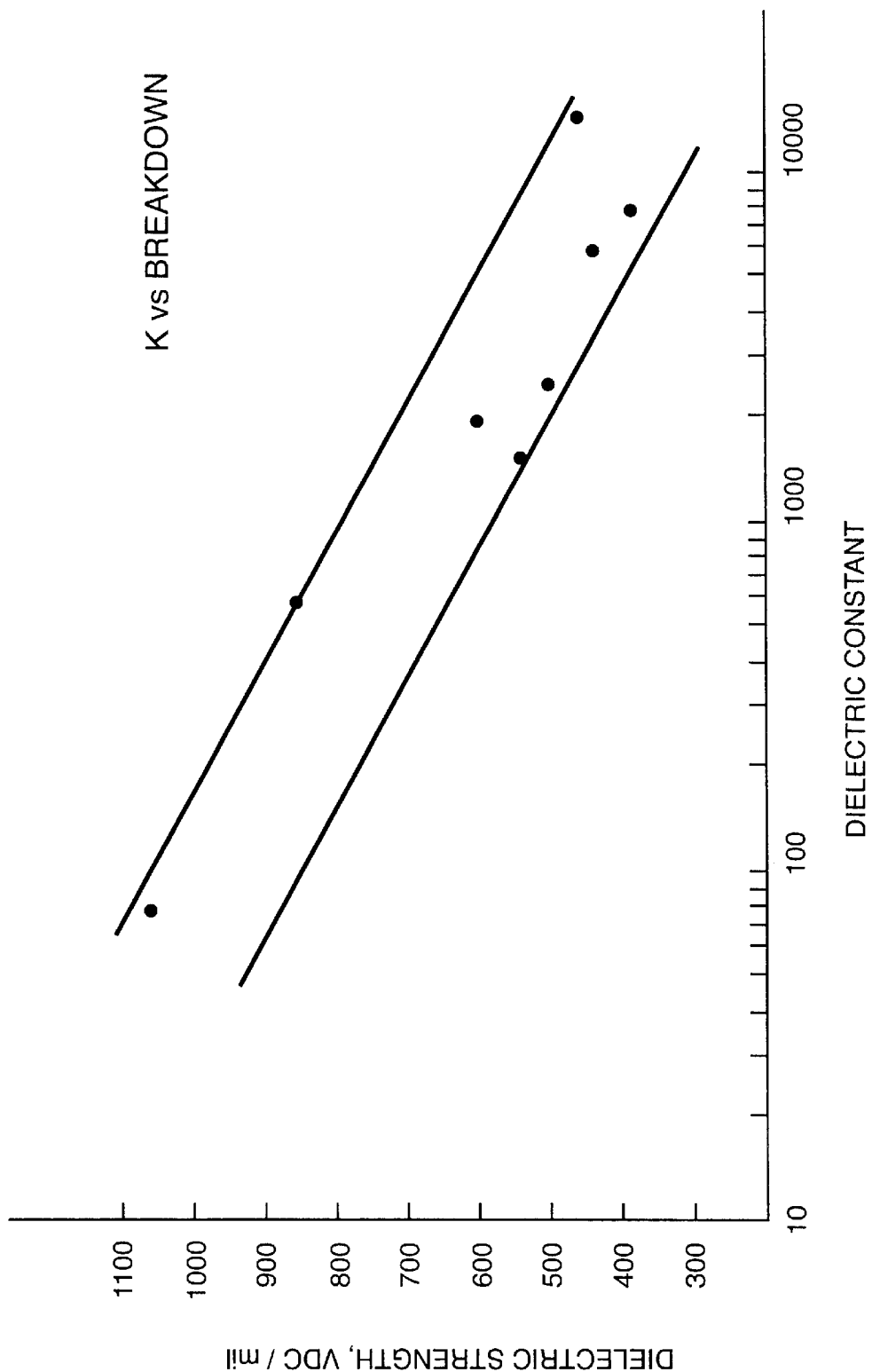
FIG. 13 is a graph illustrating K verses breakdown characteristics of prior art ceramic dielectric materials.
Figure 19:
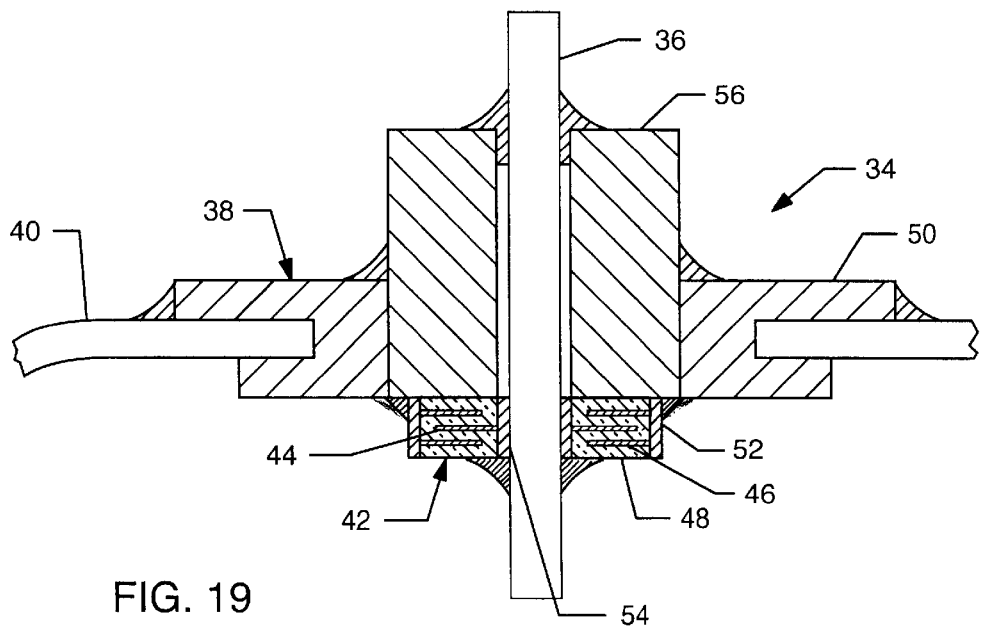
FIG. 19 is a sectional view of an EMI filter assembly similar to that shown in FIG. 2, but utilizing the capacitor of FIG. 18.

FIG. 19 uses the same prior art hermetic terminal 38 as previously illustrated in FIG. 2. However, as can be seen, by using the technology of the present invention, the ceramic capacitor 142 can be much smaller in physical size.

FIGS. 20–24 illustrate a prior art internally grounded capacitor. There, the feedthrough filter capacitor 58 comprises a monolithic, ceramic internally grounded bipolar feedthrough filter capacitor 60 having three 62, 64 passageways extending therethrough. The outer two passageways 62 are configured to receive therethrough respective conductive terminal pins 66 and 66', and the internal diameter of the first passageways 62 are metallized to form a conductive link between the first sets of electrode plates 68 and 68'. As is well understood in the art, the first sets of electrode plates 68 and 68' are typically silk-screened onto ceramic plates forming the feedthrough filter capacitor 60. These plates 68, 68' are surrounded by an insulative ceramic material that, for purposes of the present invention, need not be metallized on its exterior surfaces.

Similarly, a second set of electrode plates 70 is provided within the feedthrough filter capacitor 60. The inner diameter of the central or second passageway 64 through the feedthrough filter capacitor 60 is also metallized to conductively connect the second set of electrode plates 70, which comprise the ground plane of the feedthrough filter capacitor 60. The second passageway 64 is configured to receive therethrough the ground lead 72 which, in this particular embodiment, comprises a ground pin.

With reference to FIG. 20, the terminal pin subassembly 74 comprises a plate-like conductive ferrule 76 having three apertures therethrough that correspond to the three passageways through the feedthrough filter capacitor 60. The conductive terminal pins 66' are supported through the outer apertures by means of an insulator 76' (which also may be hermetic), and the ground pin 72 is supported within the central aperture by a suitable conductor 78 such as solder, an electrically conductive thermosetting material or welding/brazing.

The feedthrough filter capacitor 60 is placed adjacent to the non-body fluid side of the conductive ferrule 76 and a conductive attachment is effected between the metallized inner diameter of the first and second passageways 62 and 64 through the feedthrough filter capacitor 60 and the respective terminal pins 66 and ground lead 72. As was the case described above in connection with the attachment of the ground lead 72 to the conductive ferrule 76, the conductive connection between the terminal pins 66 and the ground lead 72 with the feedthrough filter capacitor 60 may be effected by any suitable means such as a solder or an electrically conductive thermosetting material or brazing. The result is the feedthrough filter capacitor assembly 58 illustrated in FIG. 24.

A novel aspect of this technology is that there is very low mechanical and thermal stress placed on the capacitor due to the fact that it floats on the leads and does not directly attach to the titanium ferrule. The titanium ferrule is designed for laser welding into the pacemaker or medical device can and is therefore, in prior art devices, subject to a great deal of thermal and mechanical stress. However, with the novel internal ground technology, the ceramic capacitor does not see these stresses and accordingly can be much weaker in overall mechanical strength. This means that for the present invention that this is a preferred embodiment whereby the very high K dielectric material with a 37° C. Curie point would be structurally very weak. However, when used with an internally grounded feedthrough the strength of such capacitor is no longer a major design consideration.

Figure 25:
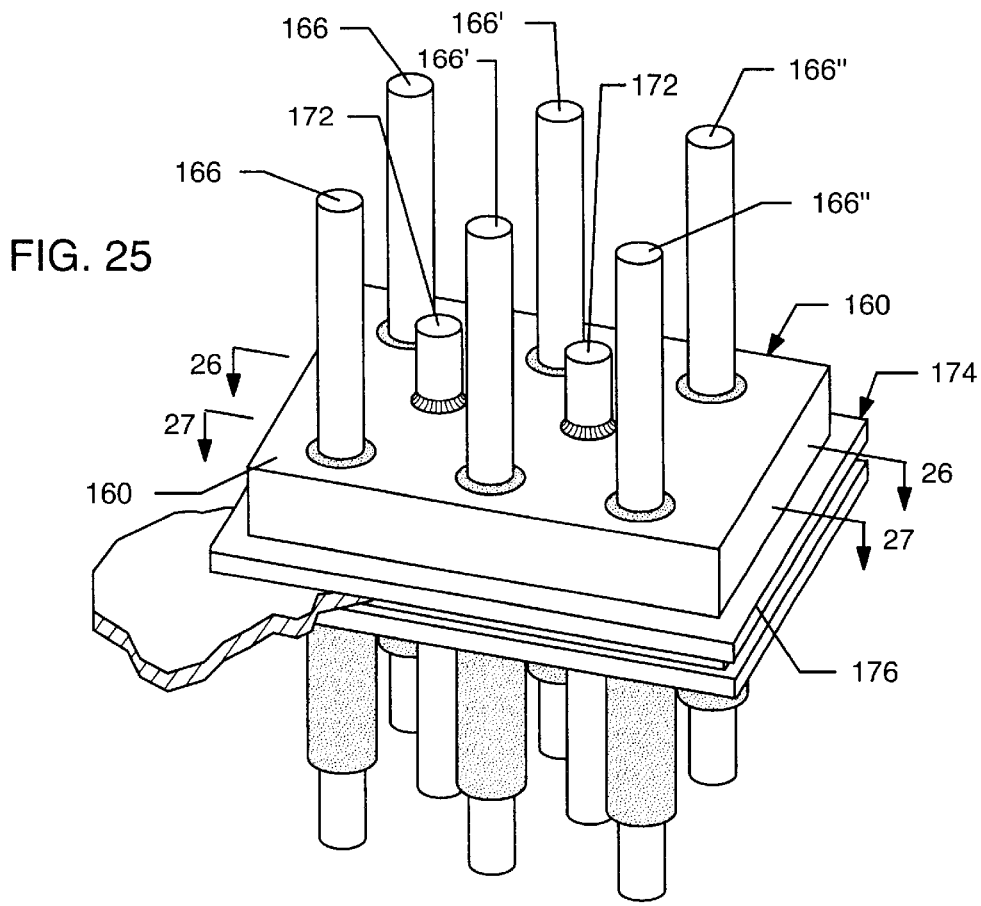
FIG. 25 is a perspective view of another hermetic terminal similar to that shown in FIG. 20, but designed for use in connection with a capacitor embodying the present invention and having the same form factor.
Figure 26:
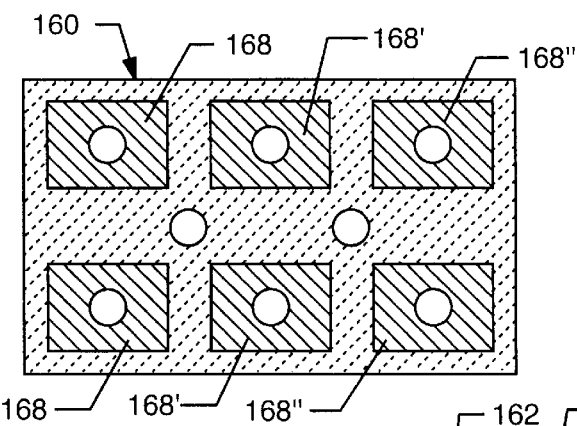
FIG. 26 is a sectional view similar to FIG. 22, illustrating the active electrode plate pattern of the six-pole capacitor of FIG. 25.
Figure 27:
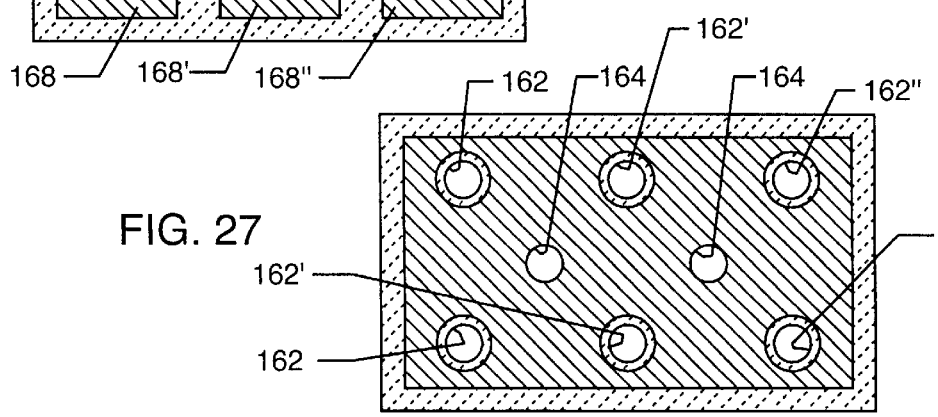
FIG. 27 is a sectional view illustrating the ground electrode plate for the capacitor of FIG. 25.

FIGS. 25–27 illustrate an aspect of the present invention in that, in the same space as the bipolar capacitor of FIG. 24, a six lead (hexpolar) capacitor can be designed with the same capacitance value and same voltage ratings (a three times improvement in package density). Functionally equivalent elements are given the same reference number increased by 100. This is a particularly important embodiment in light of the new bi-ventricular pacemaker and ICD devices that have been recently introduced to the market to control the ravages of congestive heart failure. These new devices feature more lead wires so that both ventricles (and the right atrium) can all be pulsed. In the drawings FIGS. 25–27, functionally equivalent elements shown in FIGS. 20–24 are represented by the same reference number increased by 100.

During manufacturing and testing of the feedthrough capacitor EMI filters it would be necessary to provide mathematical offsets to grade for capacitance and other electrical properties. This would be easy to do because the operation at 37° C. is readily predictable through measurements and temperature chambers and the like. In addition, the ultimate customer that manufactures the implantable medical device would need to be educated to make similar adjustments or offsets of the various electrical properties of the device. For example, at 25° C. the capacitance might be 14,000 picofarads, but actually increase to 20,000 picofarads at actual body temperature.

A major advantage of the present invention is that it would be possible to put much more capacitance in the present volume allowed for the feedthrough capacitor EMI filters used in conjunction with the hermetic terminals of an implantable medical devices. As previously mentioned, at present, prior art feedthrough capacitor EMI filters are only effective over the frequency range of 200 MHz to 3000 MHz. By greatly increasing the capacitance value, one can increase not only the attenuation of the EMI filter, but also lower its cutoff frequency. By definition, the cutoff frequency of a low pass EMI filter is its 3 dB attenuation point. By greatly increasing the capacitance value, we could move the 3 dB point down to as low as a few hundreds of kilohertz.

In this way, the EMI filter based on high dielectric constant materials would provide effective immunity against electronic article surveillance systems, frequencies used to control remote airplanes, helicopters and boats, police radio, and many other emitters that occur in the HF, VHF and UHF frequency ranges. This is particularly important in light of many reports received by the FDA of interactions between Electronic Article Surveillance Systems (EAS)(aka: retail store security systems with pedestals) and implanted medical devices. Accordingly, there is a need for much higher capacitance value EMI filters to provide effective attenuation at the frequencies at which EAS systems operate which can be as low as 58 kilohertz.

One of the reasons that the high K dielectrics as described herein are uniquely suited to human implant applications is that the human implant application is very unique. This is based on the fact that human body temperature is very stable and is centered right at 37° C. Another reason that these dielectrics are uniquely suited to most human implant applications is that these devices operate at extremely low voltages. Accordingly, volts/mil stress is really not an issue in a cardiac pacemaker that is putting out an output pulse of only 2 volts. The same is true for neurostimulators and cochlear devices, which operate in the microvolt region. It is also true of all pacemaker and ICD sense circuits which are detecting very low voltage level inter-cardiac signals in the microvolt to millivolt ranges.

A unique application is in the output circuit of an implantable cardioverter defibrillator. A cardioverter defibrillator for most of the time is sitting in a sensing mode with literally no output voltage being supplied to its ventricle output lead wires. When the implantable cardioverter defibrillator detects a dangerous heart arrhythmia such as ventricular fibrillation, it will charge up a high-energy storage capacitor and deliver high voltage shock therapy to the heart. It has been shown that high voltage application and fast rise time high voltage therapy will re-polarize the heart and cause it to go back into normal sinus rhythm.

Figure 28:
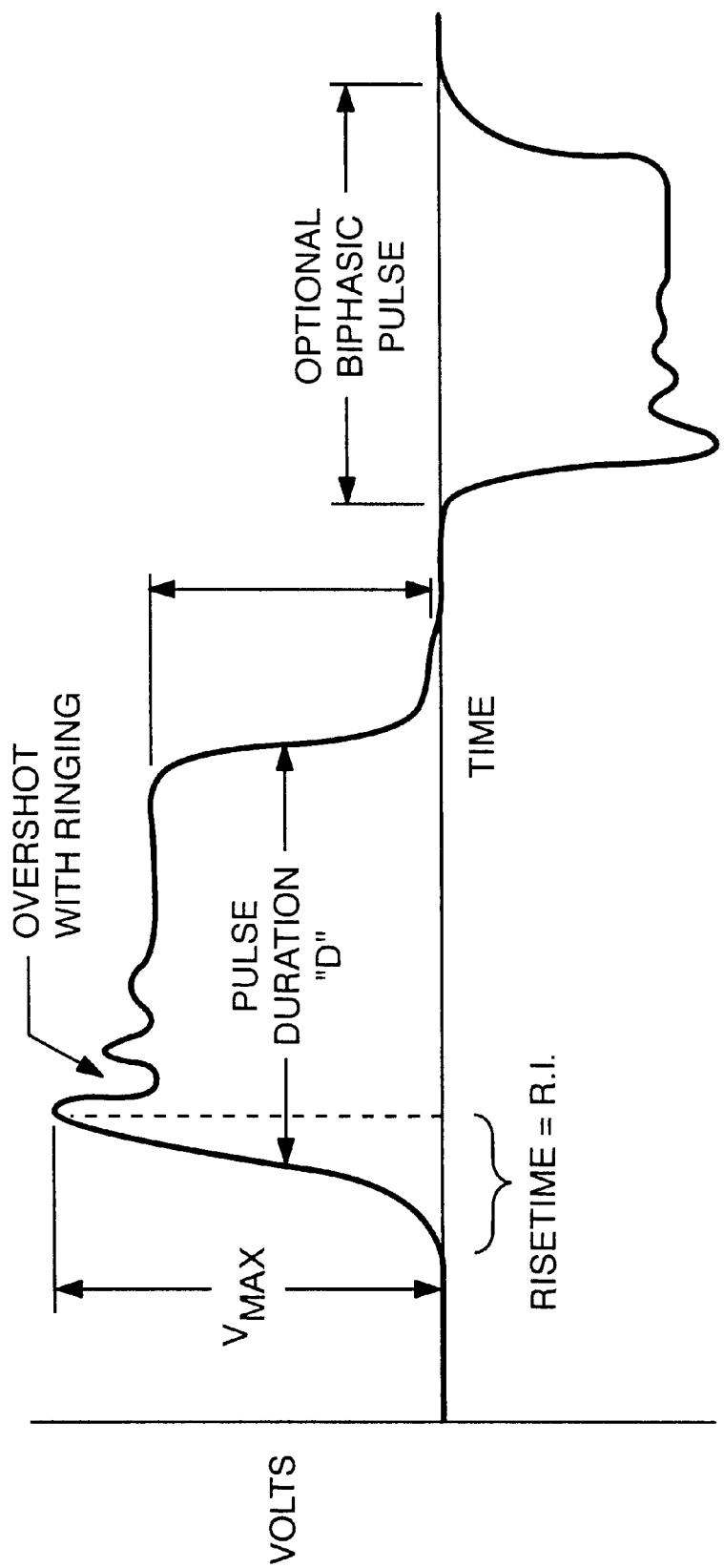
FIG. 28 is a graph showing a typical bi-phasic pulse which represents the therapeutic output of an implantable cardioverter defibrillator.

FIG. 28 represents a typical bi-phasic pulse which represents the therapeutic output of an implantable cardioverter defibrillator. V-Max typically varies from 750 volts all the way up to about 1200 volts and the pulse duration is typically in the order of 20 milliseconds. As previously illustrated by FIG. 10, high K dielectrics are extremely sensitive to applied voltage. That is, they drop drastically in dielectric constant in the presence of such high voltage stress measured in volts per mil. It is a novel aspect of the present invention that a 37° C. Curie point dielectric specifically designed without Curie point depressors could be used to have a very high K and accordingly a very high volumetric efficiency at body temperature only. It is also desirable for the capacitor to drop drastically in capacitance during the output discharge of an implantable cardioverter defibrillator. This is because charging up the capacitor dissipates energy and therefore shortens battery life. It is also important that the output of the implantable defibrillator's solid-state electronics not be overloaded with too much capacitance. This tends to interrupt their timing and in some cases can completely preclude the proper operation of the high voltage output circuitry. Accordingly, it is a novel aspect of the present invention that the capacitance value will drop drastically during the application of the high voltage shock therapy. As an EMI filter this is not important. A typical implantable defibrillator spends most of its time not delivering therapy, but monitoring patient ventricular activity. If a dangerous ventricular arrhythmia is detected, the implantable defibrillator charges up its high energy storage capacitor and then delivers the high voltage single or bi-phasic shock.

Figure 29:
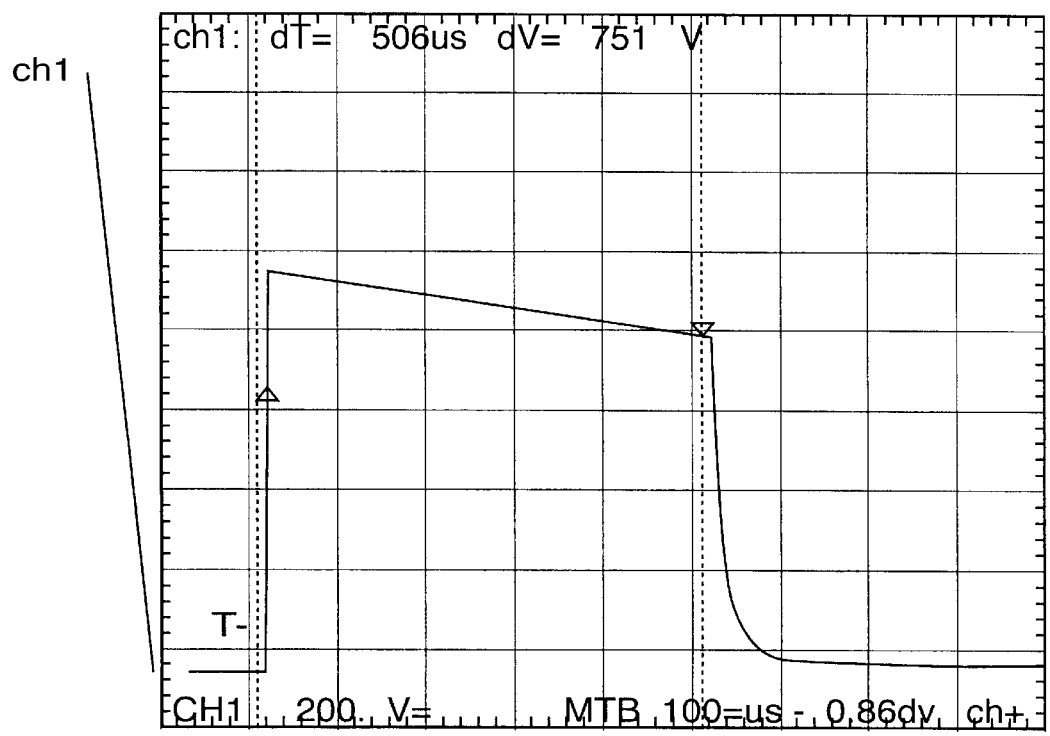
FIG. 29 is an enlarged view of an actual output pulse of an implantable defibrillator.

A close up view of an actual output pulse of an implantable defibrillator is shown as FIG. 29. As one can see, it has a very fast rise time and tends to have a droop over its 20-millisecond pulse width. Resistance to electromagnetic interference is only important when the device is not delivering its therapeutic energy, which is most of the time. However, when it is sensing cardiac activity the bias voltage on the feedthrough capacitor element is only a few millivolts. Accordingly, one will have the full benefit of the high dielectric constant in that it will be operating at a single temperature at which the dielectric constant has been optimized and also at a very low voltage bias such that it will not have a drastic drop in K and capacitance due to applied volts/mil stress. Accordingly, the use of extremely high K dielectrics which has not been previously contemplated in implantable medical devices turns out to be ideally suited for installation in an EMI filter in the output of an implantable defibrillator particularly when combined with internal ground techniques.

Unfortunately, in the past or in the prior art it has not been possible to place high capacitance value EMI filters on the output of implantable cardioverter defibrillator high voltage output circuits. The reason for this is that the capacitance loads down the output of the device and degrades the pulse. It has also been shown that the placement of the capacitor at this point can disrupt the timing of the sensitive high voltage switches thereby interfering with the proper bi-phasic waveform that is produced. It is also not energy efficient to charge up and then discharge a large value feedthrough capacitor as this dissipates energy during each cycle due to the capacitor's equivalent series resistance (ESR). A typical bi-phasic waveform has a rise time of as fast as 50 to 80 nanoseconds and a pulse width of approximately 10 milliseconds (see FIGS. 29 and 30). During a very short rest period, the pulse goes negative with a similar rise time and width. The positive and negative amplitudes of the pulse vary between 750 volts and 850 volts applied directly to cardiac tissue (with inductive ringing or overshoot, the amplitude can reach 1400 volts). It is a unique aspect of the present invention that a very high dielectric constant material be used which is very intentionally unstable in the presence of DC applied voltage. As previously mentioned, high K dielectric materials drop drastically in the presence of high volts/mil stress. In an electromagnetic interference filter, it is not necessary that the EMI filter operate as the high voltage discharge is being delivered. It is really important that the EMI filter provide effective/maximum attenuation while the device is sensing so that it does not inadvertently misfire due to the detection of electromagnetic interference (EMI can be confused as a dangerously fast heart rate caused by ventricular fibrillation). Therefore, the use of a very high dielectric constant material will provide a very high degree of electromagnetic interference attenuation at all important times, however, during the application of high voltage therapy, the capacitance value will drop drastically. This is actually a desirable effect in an implantable cardioverter defibrillator in that a lower capacitance value will dissipate less energy, have less effect on the bi-phasic waveform and less tendency to disrupt the timing circuits that control the high voltage switches.

Although an embodiment of the invention has been described in detail for purposes of illustration, various modifications may be made without departing from the spirit and scope of the invention. Accordingly, the invention is not to be limited, except as by the appended claims.

What is claimed is:

1. A feedthrough filter capacitor assembly for use in an active implantable medical device, comprising:

at least one conductive terminal pin;

a feedthrough filter capacitor having first and second sets of electrode plates disposed within a dielectric material having a dielectric constant greater than 7000, and a first passageway through which the terminal pin extends in conductive relation with the first set of electrode plates, wherein the feedthrough filter capacitor is optimized for operation within the range of 30° C. to 40° C.; and a conductive ferrule through which the terminal pin passes in non-conductive relation.

2. The feedthrough filter capacitor assembly of claim 1, wherein the feedthrough filter capacitor is optimized for operation and 37° C.

3. The feedthrough filter capacitor assembly of claim 1, wherein the dielectric constant of the dielectric material is within the range of 8500 to 22,000.

4. The feedthrough filter capacitor assembly of claim 2, wherein the dielectric material of the feedthrough filter capacitor includes at least one dopant used to shift the Curie point to 37° C.

5. The feedthrough filter capacitor assembly of claim 4, including a Curie point depressor for broadening the temperature bandwidth of the Curie point peak.

6. The feedthrough filter capacitor assembly of claim 4, wherein the at least one dopant is taken from the group of strontium titinate, lead titinate, zirconium dioxide, barium carbonate, zinc oxide, zinc borate, manganese carbonate, and titanium dioxide.

7. The feedthrough filter capacitor assembly of claim 2, wherein the dielectric material of the feedthrough filter capacitor includes at least one dopant used to shift the point of maximum dielectric constant to 37 degrees C.

8. The feedthrough filter capacitor assembly of claim 1, wherein the active implantable medical device is taken from the group of:

cardiac pacemakers, ICD's, hearing implants, congestive heart failure treatment devices, atrial defibrillators, bi-ventricular pacemakers, neurostimulators, brain stimulators, bladder control stimulators, artificial eyes, artificial noses, RF muscle actuators, implanted limb manipulation systems, artificial hearts, and ventricular assist devices.

9. The feedthrough filter capacitor assembly of claim 1, including an insulator disposed within the ferrule, for mounting the conductive terminal pin for passage through the conductive ferrule with the conductive terminal pin and the ferrule in non-conductive relation.

10. A feedthrough filter capacitor assembly for use in active implantable medical devices, comprising: at least one conductive terminal pin;

a conductive ferrule through which the terminal pin passes in non-conductive relation; a feedthrough filter capacitor having first and second sets of electrode plates disposed within a dielectric material having a dielectric constant greater than 7000, and a first passageway through which the terminal pin extends in conductive relation with the first set of electrode plates, wherein the feedthrough filter capacitor is optimized for operation at 37° C.; and a ground lead which extends into a second passageway through the feedthrough filter capacitor, wherein the ground lead is conductively coupled to the second set of electrode plates and the conductive ferrule.

11. The feedthrough filter capacitor assembly of claim 10, including an insulator disposed within the ferrule, for mounting the conductive terminal pin for passage through the conductive ferrule with the conductive terminal pin and the ferrule in non-conductive relation.

12. The feedthrough filter capacitor assembly of claim 10, including means for hermetically sealing passage of the terminal pin through the conductive ferrule.

13. The feedthrough filter capacitor assembly of claim 10, wherein the dielectric constant of the dielectric material is within the range of 8500 to 22,000.

14. The feedthrough filter capacitor assembly of claim 13, wherein the dielectric material of the feedthrough filter capacitor includes at least one dopant used to shift the point of maximum dielectric constant to 37 degrees C.

15. The feedthrough filter capacitor assembly of claim 14, including a Curie point depressor for broadening the temperature bandwidth of the Curie point peak.

16. The feedthrough filter capacitor assembly of claim 15, wherein the at least one dopant is taken from the group of strontium titinate, lead titinate, zirconium dioxide, barium carbonate, zinc oxide, zinc borate, manganese carbonate, and titanium dioxide.

17. The feedthrough filter capacitor assembly of claim 13, wherein the dielectric material of the feedthrough filter capacitor includes at least one dopant used to shift the Curie point to 37° C.

18. A process for manufacturing a monolithic chip capacitor for use in an active implantable medical device, comprising the steps of:

providing a dielectric material having a dielectric constant greater than 7000;

adding one of more Curie point shifters to the dielectric material to optimize the monolithic chip capacitor dielectric constant at the human body temperature of 37° C.; and processing the dielectric material with the added shifters into a finished monolithic chip capacitor having first and second sets of electrode plates disposed therein.

19. The process of claim 18, including the step of adding a dopant to broaden the Curie point peak of the dielectric material.

20. The process of claim 18, wherein the monolithic chip capacitor comprises a feedthrough filter capacitor.

21. The process of claim 18, wherein the monolithic chip capacitor is optimized for use in an electromagnetic interference filter.

22. The process of claim 18, including the step on installing the capacitor in a high-voltage defibrillator circuit of an implantable medical device.

23. The process of claim 22, wherein the dielectric material is further optimized so that during the delivery of high-voltage electrical energy, capacitance value of the monolithic chip capacitor drops to less than 65% of its initial value.

24. The process of claim 23, wherein the capacitance value of the monolithic chip capacitor drops to less than 20% of the initial value.

25. The process of claims 23, wherein the high-voltage electrical energy comprises a bi-phasic or mono-phasic fast rise time defibrillation pulse.

26. A process for manufacturing a monolithic chip capacitor for use in an active implantable medical device, comprising the steps of:

providing a dielectric material having a dielectric constant greater than 7000;

adding one or more Curie point shifters to the dielectric material to shift the point of maximum dielectric constant to 37 degrees C.;

adding a dopant to broaden the Curie point peak of the dielectric material;

optimizing the dielectric material so that during the delivery of high-voltage electrical energy, capacitance value of the monolithic chip capacitor drops to less than 65% of its initial value; and processing the dielectric material with the added shifters and dopant into a finished monolithic chip capacitor having first and second sets of electrode plates disposed therein.

27. The process of claim 26, wherein the monolithic chip capacitor comprises a feedthrough filter capacitor.

28. The process of claim 27, wherein the monolithic chip capacitor is optimized for use in an electromagnetic interference filter.

29. The process of claim 28, including the step on installing the capacitor in a high-voltage defibrillator circuit of an implantable medical device.

30. The process of claim 26, wherein the capacitance value of the monolithic chip capacitor drops to less than 20% of the initial value.

31. The process of claim 26, wherein the high-voltage electrical energy comprises a bi-phasic or mono-phasic fast rise time defibrillation pulse.

* * * * *